United States Patent [19]

Chen et al.

[11] Patent Number: 4,801,752
[45] Date of Patent: Jan. 31, 1989

[54] PREPARATION OF N-ALKYL AND N,N-DIALKYLANILINE

[75] Inventors: Po Y. Chen, Tao Yuan; Shiao J. Chu, Hsin Chu; Mei C. Chen, Hsin Diahn; Nan S. Chang, Tai-Nan; Wen C. Lin, Hsin Chu, all of Taiwan

[73] Assignee: Industrial Technology Research Institute, Hsinchu, Taiwan

[21] Appl. No.: 13,651

[22] Filed: Feb. 12, 1987

[51] Int. Cl.$^4$ .............................................. C07C 85/06
[52] U.S. Cl. ...................................... 564/401; 564/402
[58] Field of Search ................................ 564/401, 402

[56] References Cited

PUBLICATIONS

Chen, P. Y. et al. *Chemical Abstracts*, vol. 107, No. 6705h, (1987).
Chivadze, G. O. et al, *Chemical Abstracts*, vol 106, No.32432r, (1987).
Chen. P. Y. et al, *Stud. Surf. Sci. Catal.*, vol. 28 pp. 739–746 (1986).
Takamiya et al, "N–Methylation of Aniline with Methanol over Transition Metal Zeolite", Weseda University Report 21 (1975).

Primary Examiner—Glennon H. Hollrah
Assistant Examiner—John A. Sopp
Attorney, Agent, or Firm—Bert J. Lewen; Henry Sternberg

[57] ABSTRACT

The present invention relates to a vapor phase process for the production of N-alkyl and N,N-dialkylaniline by alkylation of aniline with an alcohol, preferably methanol and ethanol, in the presence of a ZSM-5 catalyst. A modified ZSM-5 catalyst has the advantage of high selectivity for N-alkylation while suppressing the formation of undesired by-products, such as toluidines. The molar ratio of silica to alumina in the catalyst is from about 20:1 to 700:1 and preferably from about 30:1 to 200:1. The silica-alumina may be modified with alkali metal, alkali earth metal or transition metal ions, preferably cesium, potassium, magnesium and iron, to form the finished catalyst. The reactants are contacted in the presence of the catalyst at a temperature of from about 300° to 500° C., at a pressure of from about 1 to 3 atmospheres, and at a molar ratio of alcohol to aniline of from about 1 to 6. The feed rates expressed as weight hourly space velocity (g feed/g catalyst/hour) are broadly from about 0.2 to 4.

12 Claims, No Drawings

PREPARATION OF N-ALKYL AND N,N-DIALKYLANILINE

BACKGROUND OF THE INVENTION

In the prior art, methylation of aniline with methanol was conducted in a batch reactor. Either sulfuric acid or phosphoric acid was used as the catalyst in the liquid-phase reaction that took place at a temperature of about 200° C. under a pressure of from 30 to 50 kg/cm$^2$. This traditional route suffers from the disadvantages of high capital cost, the corrosion of the reactor, and the need for waste acid treatment. The more recent vapor-phase technology has overcome corrosion problems and waste acid treatment but did not solve all the shortcomings associated with the liquid-phase reaction.

U.S. Pat. No. 3,558,706 discloses a process for the preparation of N-methylaniline by the reaction of 1 mole of aniline with 6 moles of methanol at 500°±50° C. at 1 atmosphere over a catalyst consisting of 4MgCO$_3$.Mg(OH)$_2$.4H$_2$O. The liquid hourly space velocity (LHSV) based on aniline was 0.3 to 1.0 hr$^{-1}$, and the optimum yield was 68%. The reaction required high temperatures, wasted methanol, and produced unimpressive results.

Japan Kokkai 74/81331 describes a process for making N,N-dimethylaniline by the liquid-phase reaction of aniline with methanol in the presence of a solid acid Al$_2$O$_3$-SiO$_2$, Y-type zeolite catalyst at 280° C. to give 98.1% N,N-dimethylaniline. In order to obtain the end product, a three hour reaction time and a reaction pressure of 150 kg/cm$^2$ was required. In addition to the disadvantages previously mentioned, these processes have limited flexibility as far as the control of the N-alkyl to N,N-dialkylaniline ratio was concerned, and therefore could not meet market demand.

The use of transition metal zeolites has also been described for the vapor phase catalytic N-methylation of aniline with methanol over a temperature range of 200° to 300° C. (Takamiya et al., "N-Methylation of Aniline with Methanol over Transition Metal Zeolite", Weseda University Report 21 (1975)). In this work, the catalysts were obtained by ion-exchanging HY zeolites with transition metal nitrate solution. The ion-exchanged Y zeolites, however, proved to be less active than the parent HY catalyst and gave poor control with regard to product selection.

DESCRIPTION OF THE INVENTION

In accordance with the present invention, a process for preparing N-alkyl and N,N-dialkylaniline by alkylation of aniline with a C$_1$ to C$_3$ alcohol, preferably methanol or ethanol, is disclosed. The catalyst employed in this process is a crystalline aluminosilicate zeolite of high silica to alumina ratio, namely, from 20:1 to 700:1, preferably from 30:1 to 700:1. Operative catalysts include ZSM-5 zeolites; particularly preferred are those modified with suitable ions of alkali metal, alkali earth metal and transition metal by impregnation or ion-exchange method. The modification regulates the acidity and pore size and provides flexibility in product selection.

The process of the invention is highly selective to the N-alkylated products, suppressing the formation of such unwanted by-products as toluidines (e.g., o-, p- and m-alkyl anilines), and provides a means of controlling the ratio of the N-alkyl and N,N-dialkyl products. In addition, the instant process can be carried out continuously and in the vapor phase at a low temperature and gives better results than processes with other solid acid catalysts at lower temperatures and pressures. The advantages of the invention as compared with conventional processes are summarized in Table A.

TABLE A

| Characteristics | Catalyst | |
| --- | --- | --- |
| | ZSM-5 | H$_2$SO$_4$, H$_3$PO$_4$ |
| Catalyst-products separation | Available | Unavailable |
| Catalyst recovery | Available | Unavailable |
| Corrosion problem | Eliminated | Severe |
| Waste acid pollution | Eliminated | Severe |
| Products selectivity | Flexible | Limited |

The ratio of the N-alkyl to N,N-dialkylaniline can be varied widely, e.g., from 0.13:1 to 6:1. This ability is of significant commercial importance because it allows the output of the plant to be altered in response to the demand of the individual products.

The zeolite ZSM-5 used in this invention is a crystalline aluminosilicate zeolite having a composition in terms of mole ratios of oxides as follows:

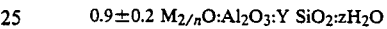
$$0.9 \pm 0.2 \, M_{2/n}O:Al_2O_3:Y \, SiO_2:zH_2O$$

wherein M is at least one cation having a valence n, Y is at least 5, z is between 0 and 40. This zeolite is further characterized by a specified X-ray diffraction pattern shown below in Table B:

TABLE B

| Interplanar Spacing d(A): | Relative Intensity |
| --- | --- |
| 11.1 ± 0.2 | s. |
| 10.0 ± 0.2 | s. |
| 7.4 ± 0.15 | w. |
| 7.1 ± 0.15 | w. |
| 6.3 ± 0.1 | w. |
| 6.04 ±0.1 | w. |
| 5.97 | |
| 5.56 ± 0.1 | w. |
| 5.01 − 0.1 | w. |
| 4.60 ± 0.08 | w. |
| 4.25 ± 0.08 | w. |
| 3.85 ± 0.07 | v.s. |
| 3.71 − 0.05 | s. |
| 3.04 ± 0.03 | w. |
| 2.99 ± 0.02 | w. |
| 2.94 ± 0.02 | w. |

These values are determined by standard techniques. The radiation is the K-alpha doublet of copper, and a scintillation counter spectrometer with a strip chart pen recorder is used. The peak heights, I, and the positions as a function of 2 times theta, where theta is the Bragg angle, are read from the spectrometer chart. From these, the relative intensities, 100 I/I$_o$, where I$_o$ is the intensity of the strongest line or peak, and d (obs), the interplanar spacing in A°, corresponding to the recorded lines, are calculated. In Table B the relative intensities are given in terms of the symbols s.=strong, w.= weak and v.s.=very strong. It should be understood that this X-ray diffraction pattern is characteristic of all the species of ZSM-5 compositions. Ion-exchange of the sodium ion with cations reveals substantially the same pattern with some minor shifts in interplanar spacing and variation in relative intensity. Other minor variations can occur depending on the silicon to aluminum ratio of the particular sample, as well as if it had been subjected to thermal treatment. (See U.S. Pat. No. 4,082,085.)

The zeolite ZSM-5, depending on the SiO$_2$ to Al$_2$O$_3$ ratio, has a surface area of from 250 to 450 m$^2$/g and a pore volume of from 0.15 to 0.35 cm$^2$/g. Its Constraint Index is 8.3. (See U.S. Pat. No. 4,350,835.) Zeolite ZSM-5 and its preparation are more particularly described in U.S. Pat. No. 3,702,886.

In accordance with the present invention, the reactant mixture is pumped, vaporized, preheated, and introduced into a fixed-bed reactor and contacted with the specified catalyst at from 300° to 500° C., preferably from 300° to 400° C., and at a pressure of from 1 to 5 atm., preferably 1 atmosphere. The molar ratio of alcohol to aniline is from 1 to 6, preferably from 2 to 4, and the weight hourly space velocity (WHSV) is from 0.2 to 4 g feed/g catalyst/hour, preferably from 0.5 to 1.6 hr$^{-1}$.

The ZSM-5 zeolites of the invention are conventionally obtained in the sodium form. By ion-exchange processes, the sodium cations may be exchanged to form zeolites having a hydrogen ion as the cation. These catalysts are referred to herein as NaZSM-5 zeolites and HZSM-5 zeolites, respectively. For example, HZSM-5 may be ion-exchanged with 0.1 M magnesium or potassium or cesium nitrate solution at 80° C. repeatedly until the maximum exchange capacity is reached. The product is then filtered, washed and dried.

The two foregoing catalysts may be impregnated with alkali metal, alkali earth metal or transition metal ions. Generally, the impregnating solution contains water-soluble salts such as nitrates or acetates and the amount of impregnated cation, based on metal oxide, is generally in the range of from 0.2 to 50%, preferably from 4 to 24%. ZSM-5 zeolite (including both NaZSM-5 and HZSM-5) is first soaked in its impregnating solution overnight, then dried and calcined at 550° C. for six hours.

In the ion-exchange process, metal ions enter the zeolite pore channels and exchange with sodium or hydrogen ions (i.e., NaZSM-5 or HZSM-5). In the impregnation process, on the other hand, the metal ions remain on the zeolite outer surface and are converted to the metal oxide in the calcination step. Both of these modification methods change the intrinsic properties of ZSM-5.

The NaZSM-5 zeolites are synthesized under conditions in which water is present in a considerable amount and frequently at elevated temperatures. This procedure is described in U.S. Pat. No. 3,702,886.

The following examples are merely illustrative of preferred embodiments of the invention. Many variations thereon may be made without departing from the spirit of the disclosed invention, as will be evident to those skilled in the art, and such variations are intended to come within the scope of what is claimed.

EXAMPLE 1

The procedure disclosed in U.S. Pat. No. 3,702,886 was adapted for the synthesis of NaZSM-5 zeolites having various SiO$_2$ to Al$_2$O$_3$ ratios. Aluminum sulfate was added to water glass and a tetrapropylammonium bromide (TPABr) solution. This was followed by a hydrothermal process to obtain the NaZSM-5 zeolites. The synthesized NaZSM-5 was treated with aqueous ammonium nitrate four times, filtered, washed, dried at 110° C. and calcined in a stream of air at 550° C. for 3 hours to obtain HZSM-5.

The prepared NaZSM-5 and HZSM-5 were used as catalyst bases for modification by ion-exchange or impregnation with nitrate or acetate salts (such as ferric nitrate, cesium nitrate, magnesium acetate) to obtain modified catalyst, referred to herein as Fe/NaZSM-5, Mg/NaZSM-5, Cs/NaZSM-5. The ion-exchange was performed by contact with 0.1 m salt solution until maximum exchange was achieved, followed by filtering, washing and drying. Impregnation was accomplished by soaking the zeolite overnight in the impregnation solution, drying and calcining for 6 hours at 550° C.

EXAMPLE 2

Table 1 shows that NaZSM-5 zeolites with different silica to alumina ratios were effective in converting aniline and methanol to N-methyl and N,N-dimethylaniline. In contrast, commercial catalyst LZ-Y52 (type NaY zeolite) and MgO showed poor activity. Amorphous SiO$_2$-Al$_2$O$_3$ showed comparable activity to NaZSM-5 (60) but a lesser selectivity for the desired products. The molar ratio of methanol to aniline was 3:1 and the WHSV was 0.8 hr$^{-1}$ in all runs.

TABLE 1

| Catalyst# | Temp. (°C.) | Aniline Conv. (%) | Selectivity (mol. %) | | |
|---|---|---|---|---|---|
| | | | N—methyl aniline | N,N—dimethyl aniline | Others |
| MgO | 420 | 13.9 | 60.1 | 2.8 | 37.1 |
| HY zeolite* | 420 | 23.7 | 80.1 | 8.4 | 11.5 |
| NaY zeolite** | 420 | 18.3 | 45.1 | 2.1 | 52.8 |
| Amorphous SiO$_2$—Al$_2$O$_3$ | 420 | 94.9 | 18.6 | 28.3 | 53.1 |
| NaZSM-5(60) | 420 | 95.6 | 16.5 | 43.2 | 40.3 |
| NaZSM-5(60) | 350 | 74.4 | 27.0 | 44.5 | 26.7 |
| NaZSM-5(100) | 350 | 72.0 | 26.2 | 60.3 | 11.8 |
| NaZSM-5(150) | 350 | 22.4 | 49.4 | 13.9 | 36.8 |
| NaZSM-5(680) | 350 | 19.2 | 46.8 | 14.2 | 39.4 |

The molar ratio of SiO$_2$/Al$_2$O$_3$ of the silica-alumina used for preparing the NaZSM-5 catalyst is shown in parentheses.
*The HY zeolite is obtained by treating NaY zeolite powder with aqueous ammonium nitrate to ion-exchange Na$^+$ for NH$_4^+$ and then filtering and washing the product and calcining at 450° C.
**Catalyst Base LZ-Y52 Powder, Linde Division, Union Carbide Co. The pore size of this catalyst is 13 angstroms.

EXAMPLE 3

Table 2 shows that the modified catalyst prepared in Example 1 exhibited excellent selectivity to N-methylaniline and N,N-dimethylaniline in the ratio of from 0.16 to 6.1. The molar ratio of methanol to aniline and WHSV were 3 and 0.8 hr$^{-1}$, respectively.

TABLE 2

| Catalyst | Modification | Temp. (°C.) | Aniline Conv. (%) | Selectivity (mol. %) | | |
|---|---|---|---|---|---|---|
| | | | | N—methyl aniline | N,N—dimethyl aniline | Others |
| Cs/NaZSM-5 (60) | Impregnated Cs$_2$O 4.3% | 420 | 59.1 | 76.3 | 18.7 | 5.0 |
| Mg/NaZSM-5 (60) | Impregnated MgO 8.5% | 300 | 88.5 | 74.8 | 22.0 | 2.3 |

TABLE 2-continued

| Catalyst | Modification | Temp. (°C.) | Aniline Conv. (%) | Selectivity (mol. %) N—methyl aniline | N,N—dimethyl aniline | Others |
|---|---|---|---|---|---|---|
| Fe/NaZSM-5 (60) | Impregnated Fe$_2$O$_3$ 8.5% | 350 | 86.0 | 20.1 | 64.4 | 15.0 |
| Mg/HZSM-5 (60) | Impregnated MgO 49.9% | 350 | 77.7 | 78.8 | 12.8 | 8.4 |
| Cs/HZSM-5 (60) | Impregnated Cs$_2$O 4.4% | 350 | 97.9 | 10.0 | 63.1 | 26.9 |
| MgHZSM-5 (60) | Ion-exchange | 350 | 93.3 | 39.0 | 45.2 | 15.8 |
| CsHZSM-5 (60) | Ion-exchange | 400 | 95.6 | 15.4 | 66.4 | 18.2 |
| KHZSM-5 (60) | Ion-exchange | 330 | 94.3 | 9.5 | 73.8 | 16.7 |
| KHZSM-5 (30) | Ion-exchange | 320 | 98.2 | 6.0 | 84.0 | 10.0 |

EXAMPLE 4

Aniline and methanol were reacted in the presence of modified ZSM-5 zeolites prepared in Example 1 with diverse operation conditions as shown in Table 3. Unless otherwise indicated, the molar ratio of methanol to aniline was 3.

TABLE 3

| Catalyst | WHSV (hr$^{-1}$) | Temp. (°C.) | Aniline Conv. (%) | Selectivity (mol. %) N—methyl aniline | N,N—dimethyl aniline | Others |
|---|---|---|---|---|---|---|
| HZSM-5(60) | 0.8 | 500 | 94.4 | 16.9 | 18.2 | 64.9 |
| HZSM-5(60) | 0.8 | 300 | 53.3 | 55.7 | 31.8 | 12.6 |
| Mg/HZSM-5 (60) | 0.8 | 300 | 70.8 | 88.6 | 10.9 | 0.5 |
| Mg/HZSM-5 (60) | 0.8 | 350 | 85.5 | 86.9 | 9.1 | 4.0 |
| Mg/HZSM-5 (60) | 0.5 | 350 | 94.9 | 69.0 | 22.9 | 8.1 |
| Mg/HZSM-5 (60) | 1.6 | 350 | 66.0 | 86.3 | 10.2 | 3.6 |
| Mg/NaZSM-5 (60) | 0.8 | 350 | 91.2 | 71.1 | 21.3 | 7.6 |
| Mg/NaZSM-5 (60) | 0.8* | 350 | 98.0 | 51.4 | 40.4 | 8.2 |
| Mg/NaZSM-5 (60) | 2.0 | 350 | 96.2 | 79.7 | 14.7 | 5.6 |
| CsHZSM-5 (60) | 0.8 | 400 | 95.6 | 15.4 | 66.4 | 18.2 |
| CsHZSM-5 (60) | 0.8 | 450 | 95.7 | 20.1 | 56.7 | 23.2 |
| CsHZSM-5 (60) | 0.8** | 400 | 97.5 | 13.1 | 78.4 | 12.1 |
| CsHZSM-5 (60) | 2.0 | 400 | 85.4 | 28.2 | 50.6 | 21.2 |

*Methanol/aniline molar ratio = 5.
**Methanol/aniline molar ratio = 4.

EXAMPLE 5

Table 4 shows that the ZSM-5 zeolites prepared in Example 1 showed distinguished activity and selectivity when compared to other solid catalysts in the alkylation of aniline with ethanol to produce N-ethyl and N,N-diethylaniline. The molar ratio of methanol to aniline was 3 and the weight hourly space velocity was 0.8 hr$^{-1}$ in all runs.

TABLE 4

| Catalyst | Temp. (°C.) | Aniline Conv. (%) | Selectivity (mol. %) N—ethyl aniline | N,N—diethyl aniline | Others |
|---|---|---|---|---|---|
| MgO | 420 | 12.1 | — | — | 100.00 |
| Amorphous SiO$_2$/Al$_2$O$_3$ | 420 | 12.5 | 11.1 | — | 88.9 |
| HY zeolite | 420 | 28.3 | 15.7 | — | 84.3 |
| NaY zeolite | 420 | 48.1 | 40.2 | 2.3 | 57.5 |
| NaZSM-5(60) | 420 | 50.8 | 51.6 | 0.7 | 47.7 |
| Mg/NaZSM-5 (60) | 420 | 58.4 | 71.6 | 6.2 | 22.2 |
| HZSM-5(60) | 420 | 57.8 | 49.2 | 6.9 | 43.9 |
| Mg/HZSM-5 (60) | 420 | 44.0 | 86.7 | 10.1 | 3.2 |

What is claimed is:

1. A process for the selective production of N-alkyl and N,N-dialkylaniline which comprises reacting in the vapor phase aniline with an alkanol having from 1 to 3 carbon atoms at a temperature of from 300° to 500° C., at a pressure of from 1 to 5 atm. in the presence of a crystalline aluminosilicate catalyst having a silica to alumina ratio of from 20:1 to 700:1, said crystalline aluminosilicate catalyst originally being possessed of Na+ cations which were ion-exchanged with H+ cations or being possessed of H+ cations which were ion-exchanged with $Fe^{+3}$, $Mg^{+2}$, $Cs^+$, or $K^+$ cations.

2. The process of claim 1 wherein said crystalline aluminosilicate catalyst is NaZSM-5 zeolite.

3. The process of claim 1 or 2 wherein said crystalline aluminosilicate catalyst is impregnated with from 0.2% to 50%, based on metal oxide, of a nitrate or acetate of cesium, potassium, magnesium or ferric.

4. The process of claim 3 wherein the amount impregnated is from 4 to 24%.

5. The process of claim 1 wherein reaction is carried out at a temperature of from about 300° to 400° C.

6. The process of claim 1 wherein the reaction is carried out at a pressure of about 1 atmosphere.

7. The process of claim 1 wherein the alkanol contains 1 or 2 carbon atoms.

8. The process of claim 1 wherein said molar ratio of alkanol to aniline is from about 1 to 6.

9. The process of claim 8 wherein said molar ratio is from about 2 to 4.

10. The process of claim 1 wherein the weight hourly space velocity is from about 0.2 to 4.

11. The process of claim 10 wherein the weight hourly space velocity is from about 0.5 to 1.6.

12. A process for the selective production of N-methyl and N,N-dimethylaniline which comprises reacting in the vapor phase aniline with methanol at a temperature in the range of from 300° to 400° C. at a pressure of about 1 atmosphere in the presence of a ZSM-5 zeolite catalyst wherein said catalyst contains sodium or hydrogen cations impregnated with cesium, magnesium, ferric or potassium ions.

* * * * *